United States Patent [19]

Ward, Jr. et al.

[11] Patent Number: 5,100,801
[45] Date of Patent: Mar. 31, 1992

[54] DEVICE FOR SEQUENTIAL MICROBIAL ENRICHMENT IN A SINGLE APPARATUS

[75] Inventors: N. Robert Ward, Jr.; Philip J. Lozier, both of Seattle, Wash.

[73] Assignee: BioControl Systems, Inc., Bothell, Wash.

[21] Appl. No.: 302,009

[22] Filed: Jan. 26, 1989

[51] Int. Cl.$^5$ .................. C12M 1/24; B01L 3/00
[52] U.S. Cl. .................. 435/296; 435/286; 435/243; 435/813; 435/819; 435/800; 435/311; 422/99
[58] Field of Search ............ 435/7.1, 284, 286, 292, 435/293, 296, 311, 313, 800, 801, 802, 819, 6, 243, 813; 422/99, 61; 141/285, 44, 39, 40, 46

[56] References Cited

U.S. PATENT DOCUMENTS

| | | | |
|---|---|---|---|
| 2,485,739 | 10/1949 | Johnstone | 422/99 |
| 2,675,951 | 4/1954 | Oriol | 141/46 |
| 4,184,916 | 1/1980 | Tolbert et al. | 435/286 |
| 4,299,091 | 11/1981 | Carter et al. | 141/46 |
| 4,888,294 | 12/1989 | Van Wezel et al. | 435/286 |
| 4,948,736 | 8/1990 | Kobayashi et al. | 435/813 |

OTHER PUBLICATIONS

Wang et al., Fermentation and Enzyme Technology, John Wiley & Sons, N.Y., p. 100 (1979) (see Fig. 7.2).
Fisher '86 Catalog, p. 731.

Primary Examiner—David L. Lacey
Assistant Examiner—William Chan
Attorney, Agent, or Firm—Seed and Berry

[57] ABSTRACT

There is disclosed an apparatus, a device, and a method using the inventive device and apparatus for the sequential enrichment of a particular microorganism to a threshold level to allow for its detection. The use of the apparatus for sequential microbial enrichment shortens the time period normally spent to enrich samples to permit the growth of enough microorganisms to detect the particular microorganism(s) of interest. The invention eliminates the need for multiple manual transfers of potentially biohazardous materials.

13 Claims, 5 Drawing Sheets

DEVICE FOR SEQUENTIAL MICROBIAL ENRICHMENT IN A SINGLE APPARATUS

TECHNICAL FIELD OF THE INVENTION

The present invention relates to an apparatus, a device, and a method using the inventive device and apparatus for the enrichment of microorganisms to allow for microbial detection or isolation. The invention shortens the time period normally spent to enrich samples to permit the growth of enough microorganisms to detect the microorganism of interest and to reduce total analysis time. The invention eliminates the need for multiple manual transfers of potentially biohazardous materials, thus eliminating the risk of transfer danger in the laboratory. More particularly, this invention relates to an apparatus, a device, an array of devices and apparati, and methods for allowing the growth of a particular microorganism within a sample to a level sufficient for detection if the particular microorganism is present in the sample.

BACKGROUND OF THE INVENTION

The detection of bacterial pathogens in clinical, food, dairy, environmental, and water samples frequently involves growth of the particular microorganism of interest in at least two types of culture enrichment broths. Initially, the sample is added to one type of broth and then allowed to incubate for a certain period of time at a particular temperature. A volume of this broth will then be added into a second type of enrichment broth and then incubated for a certain period of time at a particular temperature. The purpose of the enrichment process is to permit the growth of extremely low levels of a pathogen in a sample to sufficient levels for detection. For example, there may be only one viable Salmonella cell in a 25-gram food sample. Thus, there is a need to allow for growth of the Salmonella to high enough concentrations to permit detection in assays, such as pure culture assays, immunoassays, motility immobilization assays, and hybridization probe assays. The most sensitive immunoassays and hybridization assays generally require the presence of at least 100,000 cells per ml and preferably 10,000,000 cells per ml in an enrichment culture.

The U. S. Food and Drug Administration recommends microbial testing of certain food products. For example, Salmonella testing of certain food products is specified in some FDA regulations. The Division of Microbiology in the Center for Food Safety and Applied Nutrition of the U.S. Food and Drug Administration endorses a Salmonella assay procedure described in Andrews et al., "Isolation and Identification of Salmonella Species," Chapter 7 in *Bacteriological Analytical Manual*. 6th Edition, Association of Official Analytical Chemists, Arlington, Va. (1984). In this procedure, at least two enrichment steps are described. The first step is a "pre-enrichment step" wherein the food sample is enriched in a nutritious, nonselective broth medium to restore injured Salmonella cells to a stable condition and to promote growth. Next, a sample of the pre-enrichment broth (i.e., first enrichment broth) is added to two selective enrichment broths (i.e., second enrichment broth), wherein the sample is further enriched in a growth-promoting medium containing selective reagents. Each selective enrichment broth allows a continued increase of Salmonella organisms while simultaneously restricting proliferation of most other bacteria. The enrichment steps described in the FDA procedure both involve manual transfer of potentially biohazardous material.

The Association of Official Analytical Chemists' (AOAC) accepted method for the detection of Salmonella in a processed food sample with an immunoassay detection procedure requires that 25 grams of food sample be placed into 225 mls of a pre-enrichment broth and incubated for 24±2 hours at 35° C. This pre-enrichment step involves placing the sample into a nutritious medium that promotes the resuscitation and growth of the pathogen. After incubation, small aliquots of the pre-enrichment broth are transferred to two selective pre-enrichment broths, each of which contains certain chemical agents that permit the growth of the pathogen of interest while impeding the growth of other competitor bacteria which may have grown to high concentrations in the pre-enrichment broth. In the case of Salmonella, a 1 ml portion of the pre-enrichment culture is transferred to 10 mls of tetrathionate broth and 10 mls of selenite cystine broth. The broths are incubated for 6 to 8 hours at 35° C. This constitutes the selective enrichment part of the procedure. A third step, a postenrichment step, is used for the purpose of further promoting the growth of the pathogen of interest and removing materials that may interfere with the detection assay. In the case of Salmonella, 1 ml from both the tetrathionate broth and the selenite cystine broth is transferred to separate test tubes containing sterile mBroth. These tubes are then incubated for 14 to 18 hours at 35° C. This step constitutes the post-enrichment part of the Salmonella procedure.

After the two or more enrichment steps have been completed, an immunoassay procedure, a hybridization probe assay, standard plating assays (i.e., pure culture assays), or a motility immobilization assay is conducted to detect the presence of the microorganism of interest.

The problem of multiple transfers of biohazardous material has long been recognized in the art. For example, Banwart, "Glassware Apparatus for Determining Motile Bacteria," *Poultry Sci.* 47:1209–1212 (1967), refers to a glass apparatus with three side U-tubes projecting into a central chamber for Salmonella assays. The side U-tubes communicate via a highly porous barrier with the central chamber containing the sample in a pre-enrichment broth. The motile Salmonella organisms were able to swim up into the side U-tubes and were able to be detected there. The benefit of the Banwart U-tube is completion of the assay, including enrichment, in about 48 hours. However, there were problems associated with the sensitivity of detection and with competing motile bacteria.

Current enrichment incubation time periods were designed around the laboratory worker's standard eight-hour work day. This usually provides for full-day or overnight incubations of each step. It is likely that some of the incubation steps do not require as long an incubation period as standard microbial procedures specify. Thus, there is a need in the art for an automated enrichment device that can reduce analysis time by not requiring a laboratory technician to make transfers during nonstandard working hours.

Current immunoassay and hybridization probe assays have increased the sensitivity level for microbial detection significantly. However, there is a need for an enrichment procedure that can be automated in order to avoid transfer of potentially biohazardous material prior to conducting the immunoassay or hybridization assay detection procedure. There is also a need for an apparatus and procedure that allows for all the enrichment steps and the detections steps to be conducted in a single chamber without transfer of biohazardous material.

SUMMARY OF THE INVENTION

The present invention encompasses an enrichment device for sequential microbial enrichment, an apparatus for sequential microbial enrichment comprising a container and an enrichment device, and a method for sequential microbial enrichment of a particular organism within a sample utilizing the inventive enrichment device. Furthermore, the present invention encompasses utilization of the inventive enrichment device for a detection step following the last sequential microbial enrichment step, thereby avoiding transfer of potentially biohazardous material. Accordingly, both microbial enrichment and detection can be conducted within a single device without transfer of potentially biohazardous samples. Moreover, the inventive enrichment device reduces analysis time and labor by automatically making the transfer steps.

The present invention encompasses an enrichment apparatus comprising a container and an enrichment device connected to a single transfer system. Preferably, the transfer system is microprocessor-controlled.

The present invention also encompasses an array comprising a plurality of enrichment apparati. The inventive enrichment apparatus may be connected to a single transfer system which controls the enrichment process conducted in each apparatus. Alternatively, individual apparati may be moved, for example, by a conveyor belt, to a single transfer system for enrichment processing. The transfer system controls the addition of broth to each enrichment device at specific time intervals and sample transfer within the apparatus. It is also within the scope of the present invention to have the transfer system move to each individual enrichment apparatus for each enrichment processing step, for example, by the use of a mechanical arm that connects to each apparatus.

The invention relates to the use of a single enrichment device that permits sequential enrichment of a particular microorganism within a sample, resulting in the growth of the particular microorganism to at least a threshold level needed for detection of the particular microorganism. In this way, the inventive apparatus obviates the need for manual transfers during the enrichment sequence, thereby reducing the biological hazards associated with microbial testing and reducing enrichment time by not being dependent on the work schedule of a laboratory technician. Additionally, the inventive device eliminates the laborious manual transfer steps involved in enrichment, thereby reducing the difficulty and time associated with microbial testing.

A further aspect of the invention relates to a method whereby a single inventive device is used for sequential enrichment of a sample for a particular microorganism, followed by detection of the microorganism within the enrichment device.

Further still, this invention relates to a method for the enrichment of a sample for a particular microorganism, followed by biological amplification of a certain molecule or molecules which are used for detection of the particular microorganism, all within the inventive device. The biological amplification may involve, for example, a method such as a polymerase chain reaction (PCR) used to increase the number of target nucleotide strands from the microorganisms for a hybridization assay as the detection procedure. This aspect of the inventive method permits sequential enrichment and detection within a single apparatus, thereby completely eliminating all manual transfers and manipulations of cultures and reagents after addition of the initial sample to the device. Furthermore, this aspect of the present inventive method eliminates the biological hazard and labor-intensive nature of bacterial pathogen detection from a variety of sample types.

The inventive apparatus for sequential microbial enrichment comprises an enrichment device and a container. The container holds a volume of liquid (broth) and contains a venting means that can be opened to allow the passage of gas or closed. The enrichment device comprises a collection chamber and a collection port, and a passageway with a first opening communicating with the collection chamber and a second opening communicating with the container. The collection port of the collection chamber is connected with the transfer system and preferably comprises a venting means that can be opened to allow the flow of a gas or closed. Preferably, the collection port also comprises a broth port for adding liquid to the collection chamber. Most preferably, the collection port contains a means for obtaining a sample from the collection chamber for detection purposes.

The collection chamber may be configured so as to allow some residual liquid to remain in the collection chamber to allow the next broth to be added to the collection chamber. The passageway allows for the transfer of liquid between the collection chamber and the container. The passageway is also involved in the formation of an air lock to prevent communication between the liquid in the collection chamber and the liquid in the container during incubation times.

The air lock is used to prevent communication between the liquid within the container and the liquid within the collection chamber. The air lock is formed in the passageway by the trapping of air between the first opening and the liquid in the container. The liquid in the container must contact the second opening distal to the passageway. An example of a passageway is an air lock chamber attached to and communicating with the distal end of the collection chamber. The air lock chamber can comprise an inverted hood formed by sealing an inverted device to extend below the first opening communicating with the collection chamber. The height of the first opening can be extended above the inverted device by means of a passage device.

Alternatively, the means for preventing communication between the liquid in the collection chamber and the liquid in the container can comprise a hood sealed to the collection chamber and extending distal to the first opening.

The air lock can be broken by applying a suction or vacuum to the collection chamber when the container vent is open. This will draw out air from the collection chamber and draw liquid into the collection chamber from the container via the passageway. Alternatively, positive pressure can be applied to the container while the collection port is open, which will force the liquid into the collection chamber via the passageway. The air lock can be reestablished by applying positive pressure into the collection chamber while leaving the container vent open, or by applying a vacuum to the container while leaving the collection port open.

The present invention also comprises an array of inventive enrichment devices and inventive apparati, as described herein. A microprocessor-controlled transfer system for the array regulates the movement of liquid and venting within each apparatus. Further, the transfer system permits sequential enrichment to be run simultaneously or independently within each apparatus of the array. Alternatively, a single microprocessor-controlled transfer system can sequentially move to connect with the collection port and container vent of each apparatus for each enrichment processing step, or the apparatus can move into contact with a transfer system using a conveyor for each enrichment processing step. In each case, a single transfer system is used to process multiple apparati.

The inventive method for sequential microbial enrichment of a particular microorganism within a sample utilizes the inventive device and comprises the steps of inoculating the sample in a first enrichment broth, incubating the first enrichment sample in the container, transferring an aliquot of incubated first enrichment broth into the collection chamber, establishing a means for preventing communication between the liquid in the container and the liquid in the collection chamber, adding a second enrichment broth into the collection chamber, and incubating the second enrichment sample in the collection chamber. The inventive method further comprises optional sequential enrichment steps. The additional enrichment steps comprise removing most of the sample in the collection chamber, adding an enrichment broth into the collection chamber, and incubating. Additional enrichment steps may be used as necessary to establish the threshold concentration of cells per ml as needed for detection.

The volume ratio of incubated first enrichment broth to selective enrichment broth in the second enrichment step is controlled by the transfer system and ranges from a 1:1 volume ratio of first enrichment broth to second enrichment broth to 1:1000. The transfer system controls the volume of first enrichment broth that is brought into the collection chamber from the container. Preferably, the volume ratio of incubated first enrichment sample to second enrichment broth in the second enrichment step is from about 1:5 to about 1:20. The volume ratios for the third and subsequent enrichment steps are from 1:1 to 1:1000. The preferred volume ratio of incubated second enrichment broth remaining in the collection chamber to third enrichment broth added to the collection chamber is from about 1:5 to about 1:20. Similarly, the preferred volume ratios of subsequent enrichment steps are from about 1:5 to about 1:20.

BRIEF DESCRIPTION OF THE DRAWINGS

The enrichment device comprises a collection chamber (10), passageway (30), and collection port. The collection port depicted in FIG. 1 comprises a broth port (14) for addition of media or broth to the collection chamber and a collection chamber vent (12) that has a valve controlled by the transfer system to seal or allow the flow of gas from or to the collection chamber. The container closure may be considered as part of the container (20) or the enrichment device.

The passageway (30) has a first opening (11) communicating with the collection chamber (10) and a second opening (31) communicating with the container. The passageway also contains a screening means (32) to remove nonmicrobial particulate matter.

When both the container vent and the collection chamber vent are opened, or when the collection chamber is pressurized when the container vent is opened, a predetermined volume of incubated first enrichment broth remains in the collection chamber. The volume remaining in the collection chamber is defined by the volume in the collection chamber below the first opening of the passageway, as shown in FIG. 3. This procedure also reestablishes the air lock in the passageway to prevent communication between the liquid in the container and the liquid in the collection chamber.

In FIG. 4, broth is added to the collection chamber through the broth port. The container vent is closed, the collection chamber vent remains open, and the air lock remains in the passageway. This allows for incubation during the second enrichment step in the collection chamber without communication with the incubated first enrichment broth in the container.

FIG. 6 depicts another embodiment of the inventive device. The collection chamber (10) has a collection port at the proximal end consisting of a broth port (14) and a collection chamber vent (12). A passageway (30) in the form of an inverted hood is fused to the collection chamber with a first opening (11) communicating with the collection chamber and a second opening (31) communicating with the container. Please note that the passageway second opening is distal to the first opening, which forms an air lock when the collection chamber vent is closed.

DETAILED DESCRIPTION OF THE INVENTION

The present invention is a device, an apparatus, and a method for sequential microbial enrichment in a single apparatus that eliminates the need for transfer of potentially biohazardous material and is a labor-saving device. A further aspect of the invention is a method for using the inventive device or apparatus for the sequential enrichment of a sample for a particular microorganism, followed by the detection of the particular microorganism either within the inventive device or outside of the device with a single transfer.

Further still, the present invention relates to the sequential enrichment of a sample for a particular microorganism or microorganisms, followed by biological amplification of a certain molecule or molecules which are used for detection of the microorganism within the inventive device or outside of the device.

Sequential microbial enrichment can be accomplished with the inventive device assembled in multiple arrays, wherein many samples are simultaneously enriched when together connected to a microprocessor-controlled transfer system. The number of apparati that can be simultaneously controlled within the array depends upon the maximum capabilities of the transfer system if an array of apparati is connected to a single transfer system. Alternatively, an independent transfer system can be connected to each apparatus to effect sample transfer within the apparatus. Further, a large number of apparati can be moved to a single transfer system via a conveyor system or robotics arm to effect liquid transfer.

The inventive apparatus for selective microbial enrichment comprises an enrichment device and a container. The container holds a volume of liquid and contains a venting means (container vent) that can be opened to allow the passage of gas or closed to pressurize the collection chamber. The container may also have a means for sealing the container, such as a cap that contains the container vent. The enrichment device comprises a collection chamber and a collection port, and a passageway having a first opening communicating with the collection chamber and a second opening communicating with the container.

The collection port comprises a collection chamber vent and, preferably, a broth port. The collection port of the collection chamber is connected with the transfer system, and comprises at least a venting means (collection chamber vent). The venting means can be opened to allow the flow of a gas, or closed. The broth port is opened for adding liquid to the collection chamber.

Preferably, the first opening of the passageway is located so as to allow some residual liquid to remain in the collection chamber that cannot drain out of the collection chamber. The volume of the residual liquid remaining in the collection chamber is determined by the volume in the collection chamber located below the first opening.

The passageway allows for communication between a liquid in the collection chamber and a liquid in the container when positive pressure is applied to the container. Further, the passageway forms an air lock to prevent communication between the liquid in the collection chamber and the liquid in the container when positive pressure is applied to the collection chamber.

It is also possible to add a means for screening liquid between the collection chamber and the container such that any liquid that passes between the collection chamber and the container must pass through the screening means in the passageway. Preferably, the means for screening comprises a particulate barrier. The screening material should have pore sizes large enough to allow microorganisms to pass through but small enough to entrap particulate matter, such as from about 100 μm to about 3000 μm.

A means for screening liquid passing between the collection chamber and the container or passing between the collection chamber and the assay column can be formed with a porous or screening material. The porous material can form an interference fit, or it can be injection-molded into place. The porous material acts as a barrier to large particulate materials that may be in the sample, but not to the microorganisms. Preferably, the range of pore sizes of the porous material is from about 100 μm to about 3000 μm.

The porous material permits the sample or broth to be moved into the collection chamber while minimizing the particulate matter entering the collection chamber. Examples of porous materials which can provide a means for screening include screens, frits, porous disks, porous metals, injection-molded disks, and cloth. Examples of screens and frits are the porous plastics available from Porex Technologies, Fairburn, Ga., and screening devices available from Tetko, Inc.

The dimensions of the apparatus determine the size of the sample to be enriched. Small containers, such as a test tube holding as little as 5 mls, may accommodate small samples. The miniaturized inventive device will then fit in the test tube as the container. Conversely, large samples can be accommodated in containers holding 4 liters or more. Accordingly, the size of the container and possibly the proportionate size of the device can accommodate a sample of virtually any size.

The container is sealed. For example, the container can be sealed by a threaded cap which screws into the top of the container. The threaded cap can contain the container vent. The container vent is connected to a valve controlled by the transfer system. The threaded cap may also contain the collection chamber port. The collection chamber vent is connected to a valve that is controlled by the transfer system.

The vents may be sealed with a barrier impenetrable by microorganisms but unrestrictive to the movement of gases and liquids. Examples of materials which can be used as a vent include stainless steel frits and screens, and porous plastic membrane materials, such as cellulose acetate, cellulose nitrate, and cellulose citrate.

The inventive device is designed to allow the transfer of a small aliquot (preferably approximately 1 ml) of the first enrichment broth from the container to the collection chamber after a specified period of incubation. The volume of the aliquot is determined by the volume of the collection chamber below the first opening of the passageway. Alternatively, the size of the aliquot remaining in the collection chamber is determined by the operation of the transfer system. Preferably, the size of the aliquot in the collection chamber is from about 0.5 ml to about 10 mls. Most preferably, the size of the aliquot is about 1 ml to about 2 mls.

The inventive device can be either disposable or reusable. Preferably, a reusable device is made from glass, stainless steel, or plastic materials. The device is preferably made from plastic, such as polystyrene, polypropylene, polycarbonate, polyethylene, and other polymers known to one of skill in the art. The container is preferably reusable and can be made from stainless steel, glass, or reusable plastic materials, such as polypropylene, polycarbonate, and other polymers known to one of skill in the art.

The inventive method may use the same enrichment procedures as are described in bacteriological analytical manuals, such as the AOAC Manual for Salmonella. Examples of first enrichment broths are Lactose Broth, Lauryl Tryptose Broth, Brilliant Green Water, Nutrient Broth, Brain Heart Infusion, and Buffered Peptone Water. Examples of second enrichment broths (commonly referred to as "selective enrichment broths" in publications) are Tetrathionate Broth, Tetrathionate Brilliant Green Broth, Selenite Cystine Broth, Selenite F Broth, Selenite Brilliant Green Sulfapyridine Broth, Rappaport's Broth, and Vassiliadis, Modified Rappaport's Broth. Examples of third and subsequent enrichment broths (commonly referred to as "post-enrichment broths" in publications) are M-Broth, GN Broth, and Buffered Peptone Water. Moreover, any first enrichment broth or second enrichment broth may be used as a third or subsequent enrichment broth.

The advantage of the inventive method is the ability to conduct the entire enrichment process in a single container without the need for manual transfers of potentially biohazardous materials. Moreover, the inventive method allows for the detection of the microorganism of interest (i.e., particular microorganism) within the inventive device.

During the incubation in the first enrichment broth, the first enrichment broth should not enter the collection chamber before the first enrichment incubation period is completed. The spatial arrangement of the passageway and the collection chamber provides for an air lock so long as the collection chamber vent is closed.

Figures 1, 2:
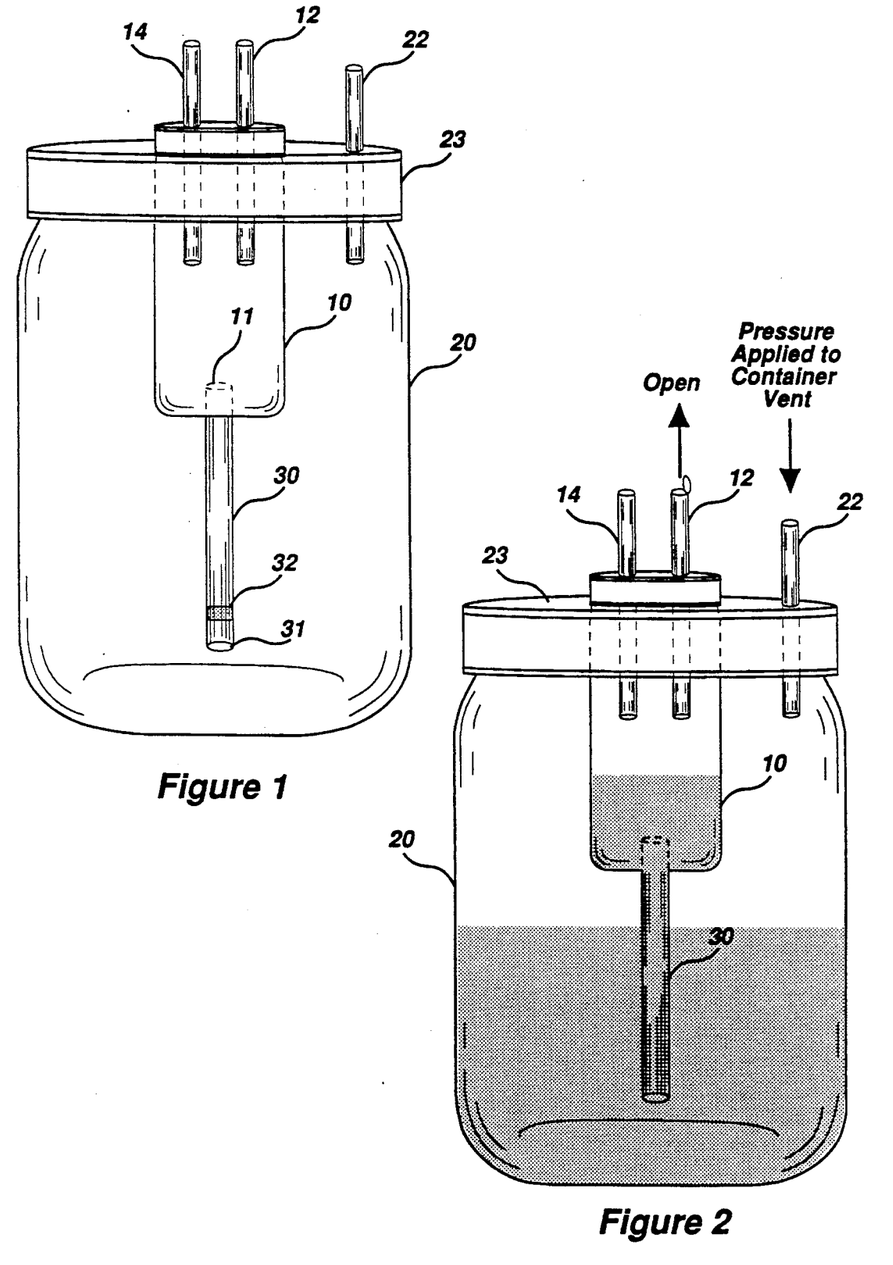
FIG. 1 depicts one embodiment of the inventive apparatus, including an enrichment device and a container (20). The container (20) holds the sample and pre-enrichment broth. The container is sealed by a closure device (23) that contains a container vent (22). The container vent will have a valve to seal or allow the passage of a gas, as controlled by a transfer system.
FIG. 2 shows the inventive apparatus during the transfer of incubated first enrichment broth from the container into the collection chamber. Liquid is brought into the collection chamber by applying positive pressure to the container vent while keeping the collection chamber vent open. Conversely, a vacuum can be applied to the collection chamber vent while leaving the container vent open.

After the first enrichment broth and sample have incubated for a specified time period at a specified temperature, some of the first enrichment sample is transferred to the collection chamber. The transfer is completed either by applying positive pressure to the container with the collection chamber vent open and allowing liquid to pass into the collection chamber, or by applying a vacuum to the collection chamber with the container vent open. The vacuum permits the first enrichment broth to enter the collection chamber. This is shown in FIG. 2.

Figures 3, 4:
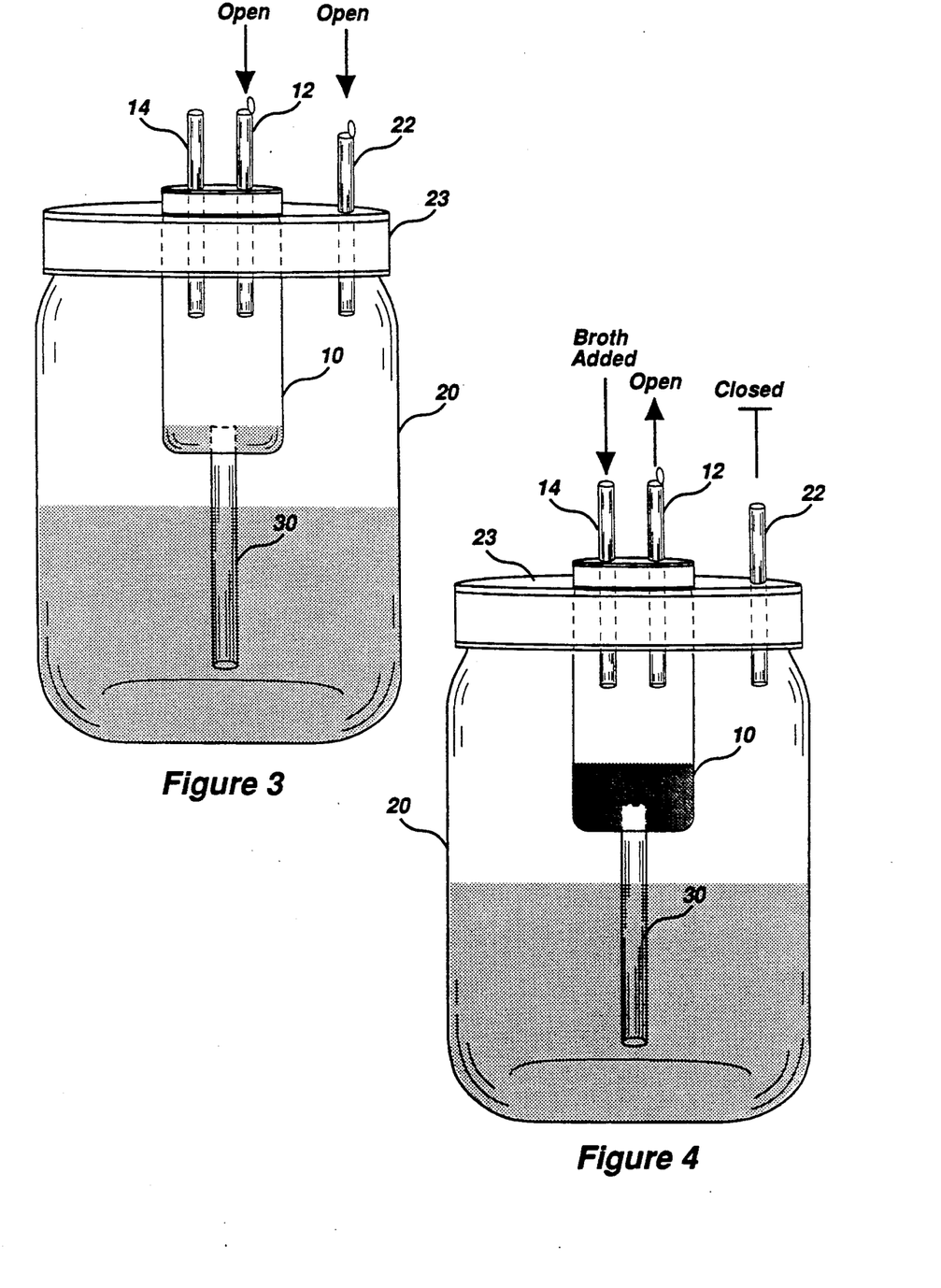

Excess first enrichment broth that may have entered the collection chamber may be removed by opening both vents as shown in FIG. 3. This excludes first enrichment broth by removing the liquid through the passageway communicating with the collection chamber. Alternatively, the collection chamber may be pressurized and the container vent opened to exclude excess enrichment broth. This leaves behind a predetermined volume of the first enrichment broth in the collection chamber.

After an appropriate volume of liquid has been left in the bottom of the collection chamber, a volume of second enrichment broth is added to the collection chamber, as shown in FIG. 4. The addition of the appropriate volume of the second enrichment broth results in the partial filling of the collection chamber.

The volume of incubated first enrichment sample to second enrichment broth in the second enrichment step is from 1:1 to 1:1000, and preferably from about 1:5 to about 1:20. Most preferably, the second enrichment broth is added such that approximately 10 volumes of second enrichment broth are present for every one volume of first enrichment broth.

The second enrichment step incubates for a specified period of time and at a specified temperature.

If a third and/or subsequent enrichment step is required, then after completion of the second enrichment step, most of the second enrichment broth can be excluded from the collection chamber. This is accomplished by applying positive pressure to the collection chamber with the container vent open, or by applying a vacuum to the container with the collection chamber vent open. Again, the air lock is not compromised, because the pressure in the collection chamber is always greater than the pressure in the container. A specified volume of the second enrichment broth is left at the bottom of the collection chamber. An appropriate volume of the third and/or subsequent enrichment broth is added. For addition of the third and/or subsequent enrichment broth, the container vent is closed and the collection chamber vent is open.

The volume ratio of incubated second enrichment broth remaining in the collection chamber to third and/or subsequent enrichment broth added is from 1:1 to 1:1000, and preferably from about 1:5 to about 1:20. Most preferably, approximately 10 volumes of third and/or subsequent enrichment broth is added to approximately 1 volume of second enrichment broth remaining.

The third enrichment broth is allowed to incubate for a specified period of time and temperature.

Additional enrichment steps may be completed as needed for the particular microbial assay.

The recommended sequential enrichment steps for several particular microorganisms are known to those of skill in the art. For example, a test for Salmonella is in the *Official Methods of Analysts*, AOAC; and the *Compendium of Methods for the Microbiological Examination of Foods*, APHA, 1984, described tests, including sequential enrichment procedures, for *E. coli*, Listeria, and Yersinia. The following table lists examples of microorganisms, enrichment steps, and possible detection assay methods. The use of the inventive apparatus and inventive method may permit a reduction of the incubation times stated in the following table.

| Microorganisms | First Enrichment | Second Enrichment | Third Enrichment | Detection Method |
|---|---|---|---|---|
| Salmonella | Lactose 24 hrs, 35° C. | Selenite-cystine Tetrathionate 24 hrs, 35° C. | — | Pure Culture |
| Salmonella | Lactose 2-4 hrs, 35° C. | Selenite-cystine Tetrathionate 6-8 hrs, 35° C. | m-Broth 14-18 hrs, 35° C. | EIA |
| Salmonella | Lactose 24 hrs, 35° C. | Selenite-cystine Tetrathionate 6-8 hrs, 35° C. | GN-Broth 14-18 hrs, 35° C. | Probe Hybridization |
| Salmonella | Trypticase Soy Broth | Tetrathionate 24 hrs, 43° C. | — | Motility Immobilization Assay |
| Listeria | UVM broth 24 hrs, 30° C. | Tryptose phosphate 24 hrs, 30° C. | — | EIA |
| E. coli | Lauryl tryptose broth, 48 hrs 35° C. | EC broth, 45-46° C. 4-8 hrs | — | Pure Culture |
| Yersinia | Trypti- | PSTA | — | Pure |

| Micro-organisms | First Enrichment | Second Enrichment | Third Enrichment | Detection Method |
|---|---|---|---|---|
| | case soy broth, 9-14 days 4° C. | broth 28° C., 2 days | | Culture |

For the detection method, EIA is "enzyme immunoassay" described herein and "pure culture" refers to standard plating assays known to those of skill in the art of microbiology and as defined in the AOAC procedures.

At the completion of the enrichment cycle, the sample is available for the detection assay. Prior to detection by hybridization techniques, it may be desirable to biochemically amplify the target molecule by known methods, such as by polymerase chain reaction (PCR) for DNA, or the "Q$\beta$" technology for RNA. Both techniques increase the number of target nucleotide strands from the microorganisms for a hybridization assay which is used for the detection of the microorganisms. The biochemical amplification step can be completed within the collection chamber, again eliminating the need for manual transfer of potentially biologically hazardous materials.

The PCR procedure can synthesize millions of copies of a specific DNA sequence in a brief in vitro reaction. PCR is a primer-directed enzymatic amplification of specific DNA sequences. The technique can be completed in a few hours, significantly facilitating all subsequent analytical procedures. The specificity of PCR amplification is based on two oligonucleotide primers that flank the DNA segment to be amplified and hybridized to opposite strands.

The PCR procedure involves repeated cycles of heat denaturation of the DNA, annealing of the primers to their complementary sequences, and extension of the annealed primers with DNA polymerase. The primers are oriented so that DNA synthesis by the polymerase proceeds across the region between the primers. The extension products of one primer can serve as a template for the other primer so that each successive cycle essentially doubles the amount of DNA synthesized in the previous cycle. This results in the exponential accumulation of the specific target fragment at approximately $2^n$, where n is the number of cycles. The termini of this discrete fragment are defined by the 5' ends of the PCR primers because each of these oligonucleotides becomes physically incorporated into one strand of the PCR product. The efficiency of PCR amplification is not significantly affected by the presence of sequences of the 5' end of the primers that are mismatched with original template DNA. Examples of PCR amplification are found in Erlich et al., "Specific DNA Amplification," Nature 331:461-62 (1988). The Q$\beta$ technology which acts to increase the number of target RNA strands is described in Lizardi et al., "Exponential Amplification of Recombinant RNA Hybridization Probes," Bio/Technology 6:1197-1202 (1988).

Figure 8:
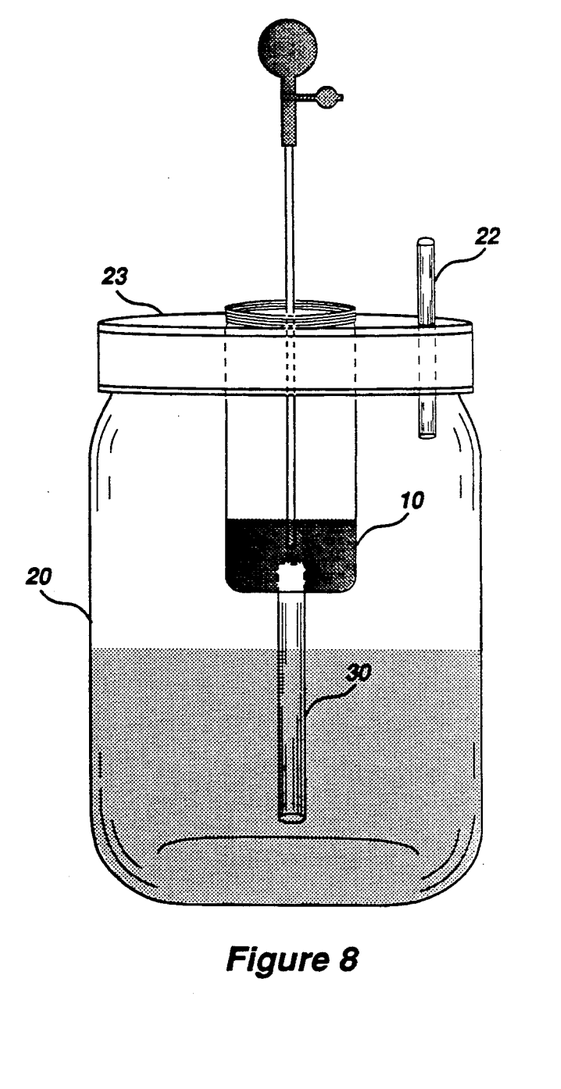
FIG. 8 shows the removal of an aliquot of final enrichment broth for detection outside of the enrichment device. The collection chamber port is removable to allow access for sampling.

After completion of enrichment and/or amplification, the microbial sample undergoes analysis for detection of the microorganism of interest. Detection techniques include pure culture assays, motility immobilization assays, immunoassays and hybridization probe assays targeting either the DNA or the RNA. The detection step can be conducted by the removal and transfer of a sample from the inventive device, as shown in FIG. 8, or by conducting the assay procedure within the device, thereby eliminating another transfer of potentially biohazardous material. Immunoassays, pure culture assays, motility immobilization assays, and hybridization probe assay techniques are known to those of skill in the art.

The inventive device can include an assay column communicating with the collection chamber. One such type of appropriate detection assay is a latex particle enzyme immunoassay. The basic format of an enzyme immunoassay is a specific binding agent, such as an antibody, attached to a solid support, such as a microtiter plate or a polystyrene bead. A test sample is exposed to the solid support and the specific analyte (antigen) will bind, if present in the sample. Nonspecific material is washed away. A detector reagent, such as a second antibody labeled with an enzyme, is allowed to bind to the analyte captured on the solid support. Any unbound enzyme-antibody reagent is washed away. Specifically bound enzyme-antibody then reacts with an enzyme substrate, which yields a color or fluorescence for visual or instrumental readout. The amount of signal produced is directly proportional to the amount of specific analyte present in the sample.

The column can be directly coated with antibody or can hold latex particles with antibodies attached to capture the antigen. Alternatively, the column can hold latex or polystyrene beads or another solid support upon which strands of nucleic acid are linked. The strands act to capture free nucleic acid target strands. An enzyme-labeled probe then binds to the captured target strands. This complex reacts with a substrate to form color or fluorescence. The column provides a large surface area for rapid reaction kinetics.

The remaining liquid in the collection chamber containing analytes to be detected can be drawn up into the column from the collection chamber, allowing the remaining liquid to come into contact with the solid support bound capture reagent in the assay column. The rest of the assay procedure can be controlled by adding reagents to the column from the proximal end via the transfer system.

Other types of detection procedures can be conducted within the inventive device, following the inventive sequential microbial enrichment method. One example of another detection system is a biochemical indicator reagent. The biochemical indicator is incorporated into the final enrichment medium of the enrichment sequence or is added after the final enrichment step. One example of a biochemical indicator reagent for Listeria is Fraser broth (Fraser et al., "Rapid Detection of Listeria soo. in Food and Environmental Samples by Esculin Hydrolysis," J. Food Protection 51:762-65 (1988)). The development of a black color with Fraser broth indicates the presence of Listeria. Other biochemical indicator reagents are known to those of skill in the art.

Multiple arrays of the inventive apparatus can be arranged such that the enrichment procedures and detection assays can be conducted with multiple samples using a single transfer system that is preferably microprocessor-controlled. Each apparatus can be located on a heating block to control the incubation temperature. Containers of second enrichment broth and possibly third and subsequent enrichment broth would be contained within the transfer system. A single microprocessor-controlled transfer system can run a plurality of samples.

Figure 5:
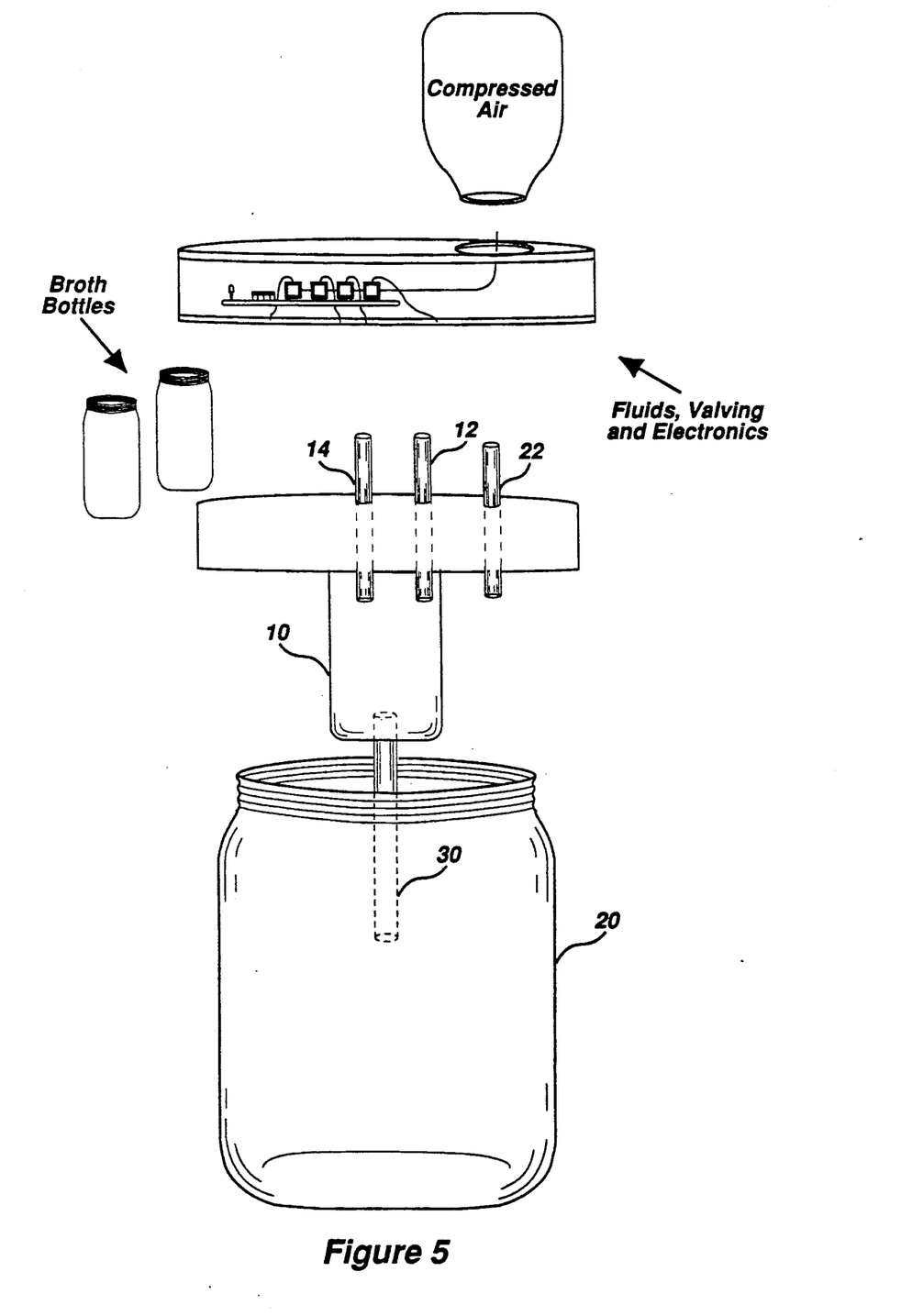
FIG. 5 depicts a schematic of the inventive enrichment device connected to one type of transfer system. The container vent, collection chamber vent, and broth port are attached to the transfer system with access to compressed air in order to facilitate sample transfer within the inventive apparatus. The transfer system also contains broth bottles for addition to the collection chamber via the broth port.
Figure 6:
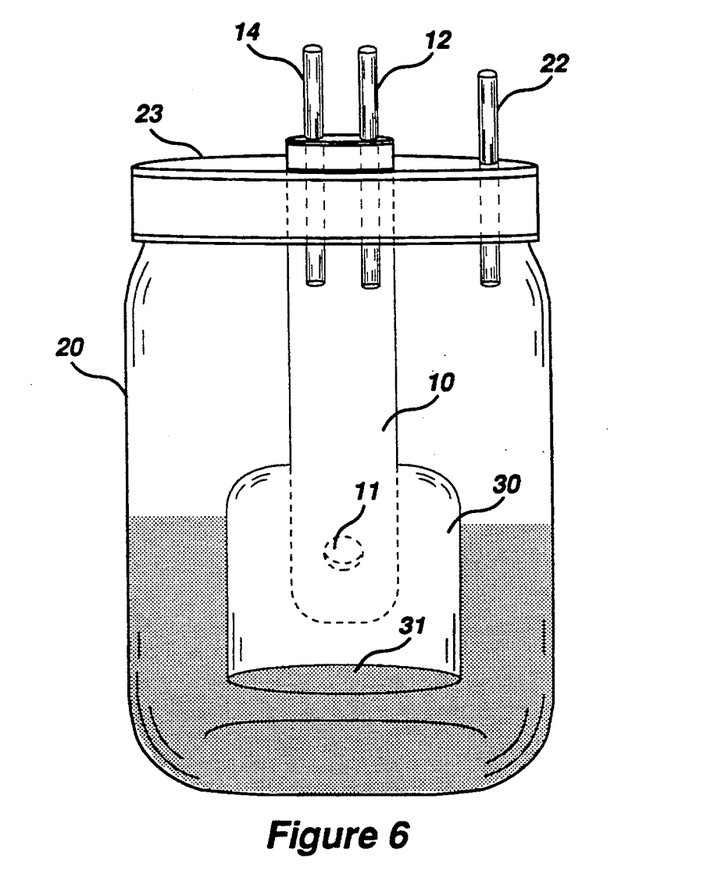
Figure 7:
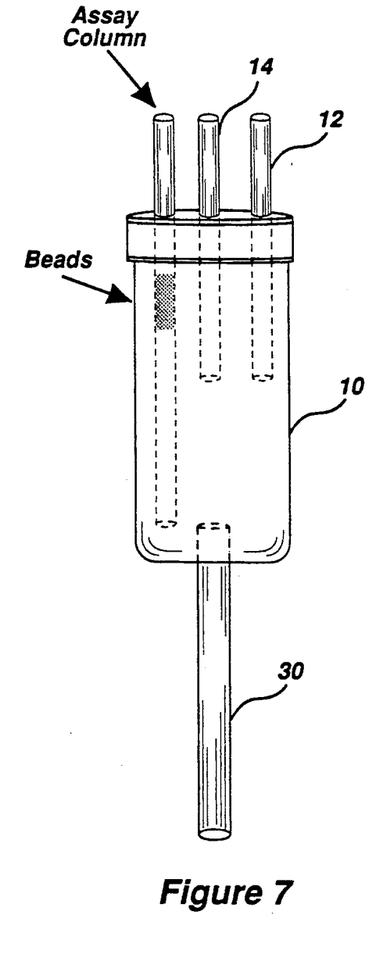
FIG. 7 shows the apparatus of FIG. 1 with an assay column extending into the collection chamber. The assay column has coated beads of an immunoassay or a hybridization assay. The assay column, broth port (14), and collection chamber port (12) comprise the collection port.

A single apparatus can have a single transfer system connected to it by the container vent and collection chamber port. For example, FIG. 5 depicts such a system.

The following examples are offered for purposes of illustration and not for limitation.

EXAMPLE I

This example illustrates an enrichment and detection of Salmonella using enzyme immunoassay procedures within the inventive apparatus. Twenty-five grams of a food sample are added to 225 ml of lactose broth in the container portion of the apparatus. The collection chamber assembly is connected to the transfer system. The enrichment device assembly is lowered into the container and sealed by tightening the assembly onto the top of the container. The collection chamber vent is closed. This results in the establishment of an air lock and prevents entry of the first enrichment broth into the collection chamber. The container vent is opened to allow the escape of microbially produced gases.

The first enrichment broth is incubated for 12 hours at 35° C. After incubation of the first enrichment broth, 1 ml or more of the first enrichment sample is brought into the collection chamber by a mechanism appropriate for the device. Excess first enrichment broth is removed from the collection chamber by pressurizing the collection chamber while keeping the container vent open. Approximately 1 ml is left in the collection chamber. In addition to removing excess first enrichment broth, this step also acts to reestablish the air lock.

About 10 ml of second enrichment broth are added to the collection chamber and mixed with the remaining first enrichment broth. This mixture incubates for 8 hours at 35° C. or 43° C., or combinations of the two temperatures. The higher temperature permits greater inhibition of bacteria which are competitors of Salmonella.

Excess second enrichment broth is removed from the collection chamber as described previously. Approximately 1 ml remains after exclusion of the excess second enrichment broth. A volume, about 10 ml, of third enrichment broth is added to the collection chamber and mixed with the remaining second enrichment broth. The post-enrichment broth incubates at 35° C. for 4 hours.

At this stage, a small aliquot of the enriched sample in the third enrichment broth can be removed and processed for detection of Salmonella in the sample by conventional microtiter formatted EIA procedure (Mattingly et al., *Food Technol.*, 1985; Swaminathan et al., *Food Technol.*, 1985).

If the EIA procedure is to be conducted within the inventive device, Salmonella antigens may be dissociated from the cell using well-known procedures, such as pH adjustment (Ibrahim et al., *J. Clin. and Microbial.* 22:1040–1044, 1985) or heating (Mattingly et al., Infra). If pH adjustment is used, a low pH solution, such as 1 N hydrochloric acid, is added to the third enrichment broth in the collection chamber through the broth port. The antigen preparation is brought into the immunoassay column by application of a slight vacuum to the immunoassay port. This vacuum acts to bring the antigen preparation to the immunoassay column which contains solid support materials (e.g., latex beads) coated with antibodies specific to the antigens of Salmonella in a manner similar to that practiced by Marshall et al., *Amer. Biotech Lab.* 5:48–53 (1987), or Foster et al., *Amer. Clin. Prod. Review* 7:32–35 (1988).

The Salmonella antigens are allowed to react with the antibodies on the solid support materials. Incubation time is preferably 3 to 30 minutes at an incubation temperature of approximately 35° C.

If excess sample in the collection chamber needs to be removed, the collection chamber is pressurized to remove all but approximately 1 ml from the collection chamber. This step provides space for the collection of reagents for the immunoassay procedure.

The immuno-column is washed with the addition of buffer (such as 1% bovine serum albumin-10 mmole phosphate-buffered saline) by the flow of the buffer through the immunoassay column. Enzyme-labeled antibodies specific for the Salmonella antigens are next added to the immuno-column and allowed to react with the antigens captured on the solid support. The enzyme-labeled antibodies incubate on the immuno-column for 3 to 30 minutes at 35° C. Unbound enzyme-labeled antibodies are washed off the immuno-column with a flow of buffered saline through the immuno-column. A substrate specific for the enzyme label, and color- or fluorescence-producing, is added to the immuno-column and allowed to incubate for 3 to 30 minutes at 35° C. The enzyme remaining on the column cleaves the substrate and produces a visually discernible color reaction or a fluorescence reaction in the immuno-column if Salmonella antigens are present in the enrichment broth. If Salmonella antigens are not present in the enrichment broth, then no color or fluorescence is produced in the immuno-column.

EXAMPLE II

This example illustrates the enrichment and detection of Salmonella using probe hybridization procedures within the inventive device. Salmonella from a 25-gram food sample is added to 225 ml of lactose broth in the container, as is described in Example I. The sequential enrichment steps described in Example I are followed. After completion of the third enrichment step, the hybridization procedure can be conducted within the inventive device or a small aliquot of the enriched sample can be removed and processed for detection of Salmonella in the sample by a DNA:DNA hybridization procedure, an RNA:ribosomal RNA (rRNA) hybridization procedure, or a DNA:rRNA hybridization procedure (Enns, *Laboratory Medicine* 19:295–300 (1988); Kohne, *American Clinical Products Review* (1986); Polsky-Cynkin et al., *Clin. Chem.* 31:1438–1443 (1985).

If a DNA:rRNA hybridization procedure is conducted within the inventive device, Salmonella are first lysed using an established procedure, such as treatment with lysozyme and detergent to release the rRNA. The lysing solution is added to the third enrichment broth in the collection chamber through the broth port. Additionally, hybridization accelerating reagents, such as dextran sulfate or polyacrylic acid, may be added. The released rRNA is brought into the hybridization column by application of a slight vacuum to the hybridization port. The vacuum acts to bring the small rRNA in contact with strands of capture DNA covalently linked to the solid support materials (e.g., latex beads). The rRNA is allowed to react with the capture strands of DNA on the solid support materials. Incubation occurs for 3 to 30 minutes at temperatures which are sufficiently stringent (preferably 35° C. to 65° C.).

The hybridization column is washed with the addition of a wash solution containing 5×SSC, 0.5% SDS, 0.5% Tween 20 at temperatures between 35° C. to 65° C. The wash solution flows through the hybridization column. Enzyme-labeled DNA probes specific for a proximal but different sequence of Salmonella rRNA not involved in the capture reaction are next added to the hybridization column and allowed to react with the rRNA captured onto the solid support. The enzyme-labeled probes incubate on the hybridization column for about 3 to 30 minutes at a temperature sufficient for the necessary stringency. Unbound enzyme-labeled probe is washed off the hybridization column with a flow of wash solution through the hybridization column. A substrate specific for the enzyme-label and color- or fluorescence-producing is added to the hybridization column and allowed to incubate for 3 to 30 minutes at 35° C. The enzyme remaining on the column cleaves the substrate and produces a visually discernible color reaction or a fluorescence reaction in the hybridization column if Salmonella are present in the enrichment broth. If Salmonella are not present in the enrichment broth, then no color is produced or fluorescence is produced in the hybridization column.

EXAMPLE III

This example illustrates the amplification of target DNA and detection of Salmonella using a probe hybridization procedure within the inventive device. The Salmonella sample is added to the inventive device and undergoes the sequential enrichment procedure as described in Example I. A lysing and denaturation solution is added to the collection chamber to release DNA from the cells. An enzymatic amplification sequence is initiated with the addition of nucleotides and DNA polymerase in appropriate buffer solutions, as taught in Erlich et al., "Specific DNA Amplification," *Nature* 331:461-462 (1988). The target DNA from the Salmonella cells is increased by approximately 10,000 times. A hybridization assay is initiated as described in Example II.

EXAMPLE IV

This example illustrates the enrichment and detection of Listeria using the inventive device for sequential enrichment and a biochemical indicator reagent incorporated into the final enrichment medium. Twenty-five grams of the food sample are added to 225 ml of a first enrichment broth, such as Trypticase soy broth, in the container. The inventive device performs sequential enrichment in a fashion analogous to that used in Salmonella enrichment, as illustrated in Example I.

The first enrichment broth incubates for 12 hours at 30° C. After incubation of the first enrichment broth, 1 ml or more of the first enrichment broth is brought into the collection chamber. Approximately 1 ml is left in the collection chamber. Approximately 10 ml of second enrichment broth, such as TSB-YE supplemented with acriflavin, naladixic acid and cycloheximide (*Federal Register* 53:211, Nov. 1, 1988), is added to the collection chamber and mixed with the first enrichment broth.

The second enrichment broth is incubated for 8 hours at 30° C. temperature. Excess broth is excluded from the collection chamber by pressurizing the collection chamber after incubation. Approximately 10 ml of third enrichment broth, containing a color-developing detection system (e.g., Fraser's broth), is added to the collection chamber and mixed with the remaining second enrichment broth. The third enrichment broth incubates at 30° C. to 35° C. The development of a black color in the third enrichment broth in 4 to 24 hours indicates a positive reaction and the presence of Listeria in the initial food sample.

The principles, preferred embodiments, and modes of operation of the invention have been described in the foregoing specification. The invention which is intended to be protected herein, however, is not to be constrained as limited to the particular forms disclosed since these are to be regarded as illustrative rather than restrictive. Variations and changes may be made by those skilled in this art without departing from the spirit and scope of the invention.

We claim:

1. An apparatus for sequential microbial enrichment, comprising a container and an enrichment device wherein the container includes a venting means and wherein the enrichment device comprises:
   a collection chamber;
   a collection port having an inlet and a vent in communication with the collection chamber;
   a passageway having a first opening communicating with the collection chamber and having a second opening communicating with the container; and
   means for creating an air lock in said passageway to prevent media inside the collection chamber from passing into the container such that microbial enrichment can take place within the collection chamber without additional media entering into the collection chamber.

2. The apparatus of claim 1, further comprising a transfer system communication with the collection chamber and the container and wherein the collection chamber is disposed inside the container such that microbial enrichment can take plate solely within the container.

3. The apparatus of claim 1 wherein the means for creating an air lock in said passageway between the container and the collection chamber includes a valve inside the venting means of the container such that when the valve is closed, air remaining inside the passageway creates an air lock in the passageway when media is introduced into the collection chamber via the inlet, the air lock preventing the media from passing into the container from the collection chamber.

4. The apparatus of claim 1 wherein the passageway comprises a portion that extends above a bottom surface of the collection chamber to maintain a predetermined amount of media inside the collection chamber below said portion.

5. The apparatus of claim 4, further comprising a means for screening the media in the passageway in between the collection chamber and the container.

6. The apparatus of claim 5 wherein the means for screening comprises a porous material.

7. The apparatus of claim 6 wherein the pore size of the porous material is large enough to allow bacteria to pass but small enough to prevent passage of particulate matter.

8. The apparatus of claim 1 wherein the collection chamber includes a means for maintaining at all times a predetermined amount of media inside the collection chamber.

9. An array comprising a plurality of sequential microbial enrichment apparati, each apparatus comprising a container and an enrichment device, wherein the container includes a venting means and wherein the enrichment device comprises:

a collection chamber;

a collection port having an inlet and a vent in communication with the collection chamber;

a passageway having a first opening communicating with the collection chamber and having a second opening communicating with the container; and means for creating an air lock in said passageway to prevent media inside the collection chamber from passing into the container such that microbial enrichment can take place within the collection chamber without additional media entering into the collection chamber.

10. The array of claim 9, further comprising a transfer system communicating with the collection chamber and the container of each enrichment apparatus of the array and wherein the collecting chamber is disposed inside the container such that microbial enrichment can take place solely within the container.

11. The array of claim 9, further comprising a single transfer system, wherein the transfer system and the enrichment device connect during processing transfer steps.

12. The array of claim 9 wherein the means for creating an air lock in said passageway between the container and the collection chamber includes a valve inside the venting means of the container such that when the valve is closed, air remaining inside the passageway, creates an air lock in the passageway when media is introduced into the collection chamber via the inlet, the air lock preventing the media from passing into the container from the collection chamber.

13. The array of claim 9 wherein the collection chamber includes a means for maintaining at all times a predetermined amount of enrichment medium inside the collection chamber of each apparatus.

* * * * *

UNITED STATES PATENT AND TRADEMARK OFFICE
CERTIFICATE OF CORRECTION

PATENT NO. : 5,100,801
DATED : March 31, 1992
INVENTOR(S) : N. Robert Ward, Jr.; Philip J. Lozier It is certified that error appears in the above-identified patent and that said Letters Patent is hereby corrected as shown below:

In column 16, claim 2, line 37, please delete "plate" and substitute therefor -- place --.

Signed and Sealed this

Fifteenth Day of June, 1993

Attest:

MICHAEL K. KIRK

Attesting Officer

Acting Commissioner of Patents and Trademarks